United States Patent [19]

Chuttani et al.

[11] Patent Number: 5,054,501
[45] Date of Patent: Oct. 8, 1991

[54] STEERABLE GUIDE WIRE FOR CANNULATION OF TUBULAR OR VASCULAR ORGANS

[75] Inventors: Ram Chuttani, North Quincy; Michael D. Apstein, Newton; David L. Carr-Locke, Chestnut Hill, all of Mass.

[73] Assignee: Brigham & Women's Hospital, Boston, Mass.

[21] Appl. No.: 524,307

[22] Filed: May 16, 1990

[51] Int. Cl.⁵ ............................................. A61B 25/01
[52] U.S. Cl. .................................... 128/772; 604/282
[58] Field of Search ............... 128/772, 657; 604/164, 604/282

[56] References Cited

U.S. PATENT DOCUMENTS

| | | | |
|---|---|---|---|
| 3,789,841 | 2/1974 | Antoshkiw | 128/772 |
| 4,538,622 | 9/1985 | Samson et al. | |
| 4,616,274 | 10/1986 | Morrison | 128/772 |
| 4,676,249 | 6/1987 | Arenas et al. | 128/772 |
| 4,799,496 | 1/1986 | Hargreaves et al. | 128/772 |
| 4,827,941 | 5/1989 | Taylor et al. | |
| 4,834,724 | 5/1989 | Geiss et al. | |
| 4,867,173 | 9/1989 | Leoni | |
| 4,867,174 | 9/1989 | Skribiski | |
| 4,886,506 | 12/1989 | Lougren et al. | 604/282 |

*Primary Examiner*—William E. Kamm
*Assistant Examiner*—Scott R. Akers
*Attorney, Agent, or Firm*—Sterne, Kessler, Goldstein & Fox

[57] ABSTRACT

A steerable guide wire for cannulation of tubular or vascular organs. The guide wire has a distal end and a proximal end. The guide wire has at least one coil forming a helix near the distal end of the guide wire to aid in the negotiation through tubular or vascular organs such as endoscopic retrograde or antegrade cannulation of the cystic duct. A removable clamp is secured to the proximal end of the guide wire to allow the user to apply torsional and longitudinal force to steer the guide wire into position.

15 Claims, 3 Drawing Sheets

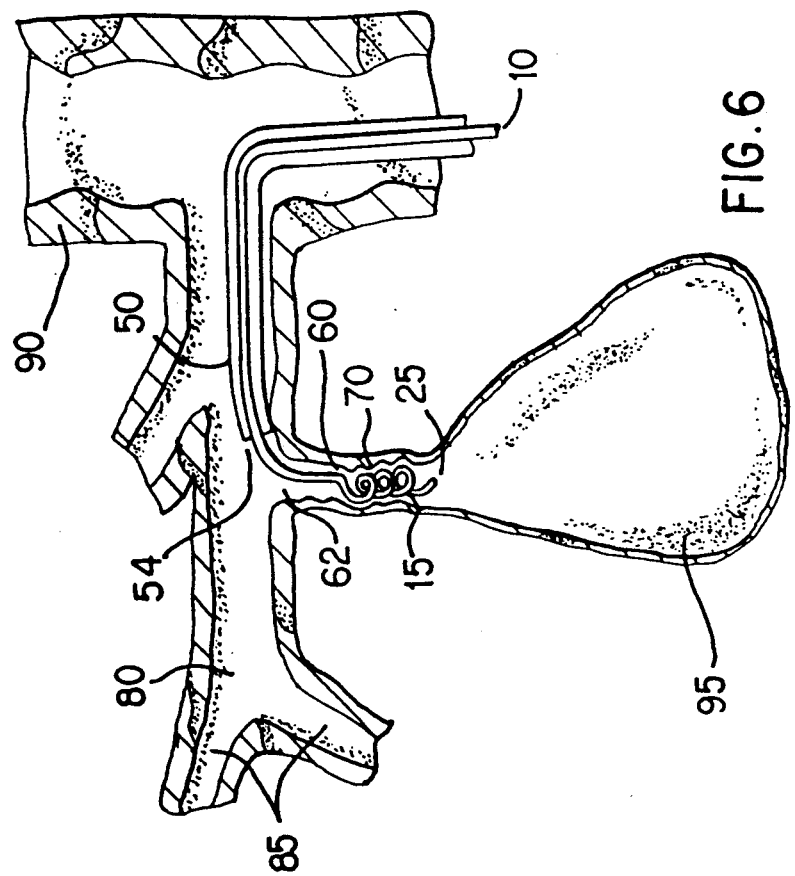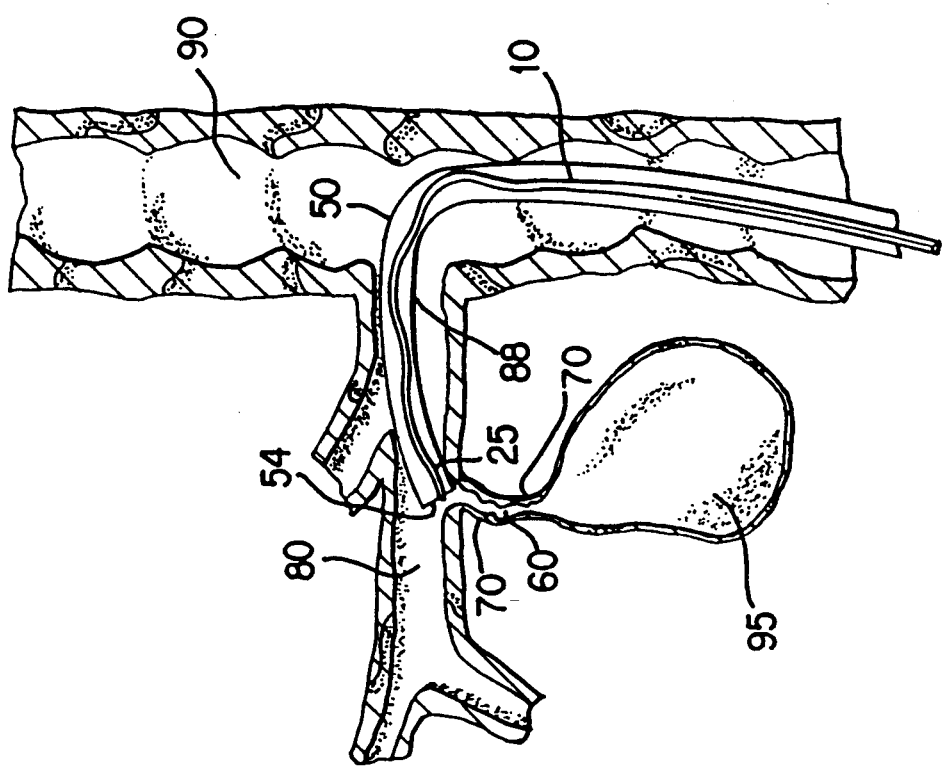

STEERABLE GUIDE WIRE FOR CANNULATION OF TUBULAR OR VASCULAR ORGANS

FIELD OF THE INVENTION

The invention relates generally to flexible guide wires for cannulation of tubular or vascular organs to be used alone or in conjunction with catheters or endoscopes.

BACKGROUND OF THE INVENTION

When medical procedures or operations require cannulation of a tubular or vascular structure or organ in the human body, guide wires are typically employed. Due to the flexibility, softness of the tip and narrow gauge of a typical guide wire, it is advantageous to first insert a guide wire into the organ to help position a larger diameter catheter or other instrument needed for the procedure. Some organs have characteristics which make the use of conventional straight guide wires difficult. For example, standard techniques using conventional guide wires for endoscopic cannulation of the cystic duct are not entirely satisfactory.

The cystic duct connects the gallbladder and the common bile duct. The cystic duct, however, has unique characteristics which distinguish it from other tubular organs. The mucous membrane lining the interior of the cystic duct has several crescentic folds commonly called valves of Heister, the exact function of which is still unclear. Typically, the number of folds ranges from five to twelve. The folds are directed and obliquely round having an appearance of a continuous spiral valve. The presence of these spiral folds, in combination with the tortuosity of the cystic duct, makes endoscopic cannulation of the cystic duct extremely difficult. The valves of Heister impede the introduction of surgical instruments and are prone to lacerations. There is a great need for a device which makes cannulation of the cystic duct both safe and easy for, among other things, the diagnosis and treatment of gallstone disease.

There has been extensive research and development committed to the design of a suitable guide wire for use in conjunction with a preshaped catheter system to allow the cystic duct and gallbladder to be reliably catheterized, retrograde, using an endoscope or other apparatus. Because of the unique structure of the cystic duct folds, successful catheterization of the cystic duct and the gallbladder during endoscopic retrograde procedures is obtainable only when favorable anatomical situations exist. Because of the difficulty in negotiating the cystic duct, it is only exceptional cases where selective catheterization can be achieved using conventional guide wires.

Frimberger et al., *Endoscopy* 15:359 (1983), was among the first to report attempts to routinely cannulate the gallbladder with the aid of a special endoscope. The system was extremely complicated, however, and did not facilitate reliable cannulation.

One of the most advanced guide wire and catheter systems for cannulation of the gallbladder and cystic duct was disclosed in Foerster et al., *Endoscopy* 20:30, 33 (1988). Foerster et al. discloses a specially made thin steerable guide wire with a straight, 6 cm long soft distal tip. In Foerster et al., the thin, straight steerable guide wire is inserted into a pre-shaped catheter pre-positioned near the opening of the cystic duct. The guide wire is then advanced through the catheter and into the cystic duct. Once positioned in the cystic duct, the thin, straight guide wire must be carefully manipulated to successfully traverse the valves of Heister. The use of a conventional straight guide wire, as taught in Foerster et al., may result in the guide wire catching on the cystic duct folds, impeding its forward progress and causing injury to the duct.

Hence, it is an object of this invention to provide a guide wire designed to be used in conjunction with a preshaped open hook configuration catheter system, as an example that described by Foerster et al., for endoscopic retrograde cannulation of the gallbladder. The unique configuration of the guide wire invention is the result of careful research into the anatomy of the cystic duct and the valves of Heister. The invention comprises guide wire having a unique construction which provides forward traction upon application of torsional force along the guide wire while at the same time employing an ultra-low friction surface which reduces friction between the guide wire and a catheter when used in conjunction.

SUMMARY OF THE INVENTION

Generally, the invention relates to a flexible, steerable guide wire for retrograde or antegrade cannulation of tubular or vascular organs such as the cystic duct. The guide wire has a proximal end and a distal end, the distal end having a unique spiral tip for negotiation of the cystic duct. More specifically, the distal end of the guide wire is formed with a plurality of coils forming a helix. The coils are formed so that the helix has an outer diameter greater than the diameter of the distal end of the guide wire when the helix is in the free position. Because the guide wire is flexible, the helix can be straightened or elongated when subject to external forces, such as those induced when the guide wire is passed into a narrow catheter, and the outer diameter of the helix can be reduced to the point where it approaches the diameter of the guide wire shaft at the distal end.

At the proximal end of the guide wire, means for manipulation of the guide wire are removably secured to facilitate transmission of torsional forces along the longitudinal length of the guide wire to help steer the guide wire into a desired position. In one embodiment of the invention, the guide wire has an ultra-low friction surface and is tapered at the distal end to increase flexibility at the distal tip.

BRIEF DESCRIPTION OF THE DRAWING

The accompanying drawings, which are incorporated in and form a part of the specification, illustrate the embodiment of the present invention and, together with the description, serve to explain the principles of the invention.

FIG. 5 illustrates the steerable guide wire inserted into a flexible catheter causing the helix to be straightened along the length of the distal end of the guide wire. The catheter and guide wire are positioned in the common bile duct with the distal tip of the guide wire near the cystic duct.

FIG. 6 shows the distal tip of the steerable guide wire negotiating the valves of Heister located in the cystic duct.

DETAILED DESCRIPTION OF A PREFERRED EMBODIMENT OF THE INVENTION

Figure 1:
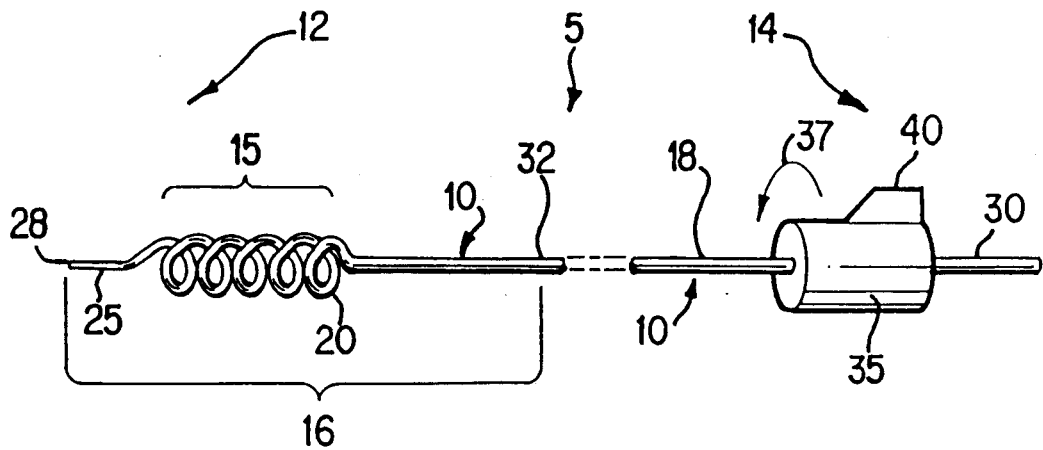
FIG. 1 is a perspective view of the steerable guide wire for cannulation of the gallbladder.

Referring to FIG. 1, the steerable guide wire, designated generally as (5), comprises a wire shaft (10) having a distal end (12) and a proximal end (14). The guide wire (5) has a total length of between 50 and 900 centimeters. The distal end (12) of the guide wire (5) has a plurality of individual coils (20) forming a helix (15) which, in the preferred embodiment, terminates into a distal tip (25) and a soft rounded end (28). To facilitate increased flexibility at the distal end, the preferred embodiment of the wire shaft (10) decreases in diameter throughout a tapered portion (16) near the distal end (12) of the guide wire (5). Of course, other structures can be used to accomplish increased flexibility at the distal end, such as a step-down configuration.

A removable clamp (35) having steering means (40) can be secured to the proximal end (14) of the guide wire (5). The removable clamp (35) can be used to steer the guide wire (5) via transmission of torsional and longitudinal force from the steering means (40) to the wire shaft (10) along its length. The removable clamp (35) is positioned near the proximal end (14) of the wire shaft (10) so that proximal surface length (30) exists on the proximal side of the removal clamp (35).

In a preferred embodiment of the invention, the length of the guide wire (5) is 400 centimeters. The wire shaft (10) is shaped having a cylindrical or other geometrically shaped cross-section and is made of a plastic or metal material having an ultra-low coefficient of friction on its outer surface. In a preferred embodiment, the wire shaft (10) can be made from a metallic or plastic wire having a hydrophilic coating such as GLIDEWIRE ™ made by Terumo [Medi-tech] of Japan, distributed by Microvasive of Watertown, Mass. Preferably, the guide wire (5) has an outer diameter of 0.035 inches (0.89 mm) with a constant taper along a tapered portion (16) at the distal end (12). The tapering begins at the taper junction (32) where the outer diameter is 0.035 inches (0.89 mm) and ends at the rounded end (28) at the extreme distal extremity of the guide wire (5) having a narrowed diameter of 0.021 inches (0.53 mm). The tapered portion (16) of the preferred embodiment has a length of 30 mm when measured from the taper junction (32) to the rounded end (28). The taper junction (32) is positioned 10 millimeters from the proximal end of the helix (15) in the preferred embodiment. Due to the reduced diameter, the tapered portion (16) allows the distal end (12) to have increased flexibility. The narrower gauge along the the tapered portion functions to allow the helix (15) to be slidably inserted into a catheter (50). When a catheter (50) is disposed over the length of the guide wire (5), the helix (15), due to its flexibility, straightens or flattens out as depicted in FIG. 2.

The helix (15) is formed using at least one coil (20). Different embodiments having different numbers of coils (20) allow the user to select the embodiment best suited for the individual patient. The varying anatomical differences in patients may dictate any number of coils forming the helix. In the preferred embodiment, five coils (20) are present. Each coil (20) in the preferred embodiment has an outer diameter from 1 to 2 millimeters, with a distance of 1 to 2 millimeters between each concentric coil (20), and the helix being 15 millimeters in length. In one embodiment of the invention, a distal tip (25) is located on the distal side of the helix (15) and terminates in a rounded end (28). In the preferred embodiment, the distal tip 925) would have a length of 5 mm. However in an alternative embodiment the guide wire (5) would terminate at the distal end with the helix (15), and would not have a distal tip (25) as shown in FIG. 1.

Figure 2:
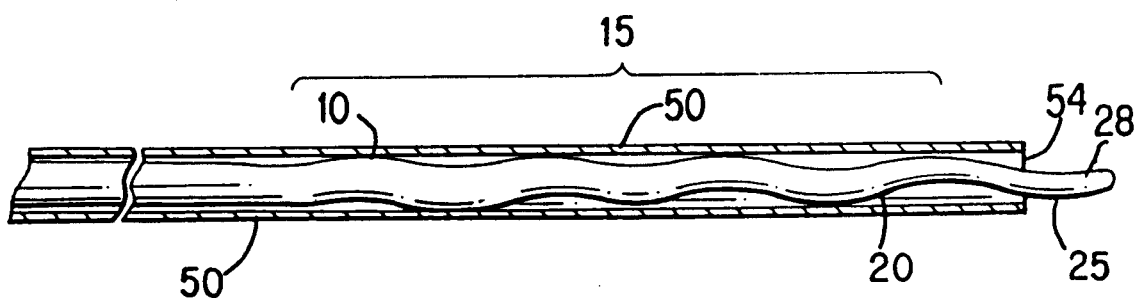
FIG. 2 is a perspective view of the steerable guide wire inserted into a preshaped common bile duct catheter so that the helix at the distal end is straightened by the dimensions of the catheter.
Figure 3:
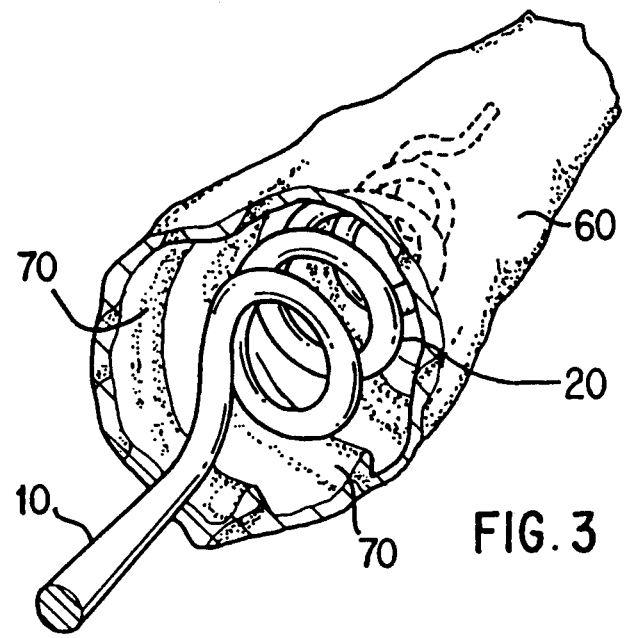
FIG. 3 illustrates the steerable guide wire negotiating the valves of Heister located in the ostium of the cystic duct.

Referring to FIG. 2, the wire shaft (10) including the helix (15) is constructed of a flexible material having an ultra-low friction surface (18) to allow the wire shaft (10) to slide easily through a catheter (50) even when the helix (15) is straightened or flattened due to the narrow internal diameter of the catheter (50). When the guide wire (5) is used in conjunction with a catheter (50), there must be minimal friction between the guide wire (5) and the catheter (50). An ultra-low friction surface may be applied to either the catheter (50) or the guide wire (5) to minimize friction. Therefore, in another embodiment of the invention, the guide wire (5) will lack any ultra-low friction surface but will be used with a catheter (50) having an ultra-low friction surface such as TEFLON or similar material. In either embodiment, however, the wire shaft (10) must be made of a material that provides good torsional rigidity required for traversing vascular structures or tubular organs such as the cystic duct.

The actual number of coils (20) selected to form the helix (15) is variable to allow different embodiments which can be used depending on the anatomy of the patient and the organ to be cannulated. The actual embodiment used would be that which provides enough forward traction through organs such as the cystic duct without slipping while at the same time minimizing friction within the catheter by keeping the number of coils to a minimum. In the preferred embodiment, the coils (20) will be constructed to spiral along the longitudinal axis in a clockwise configuration.

Figure 4:
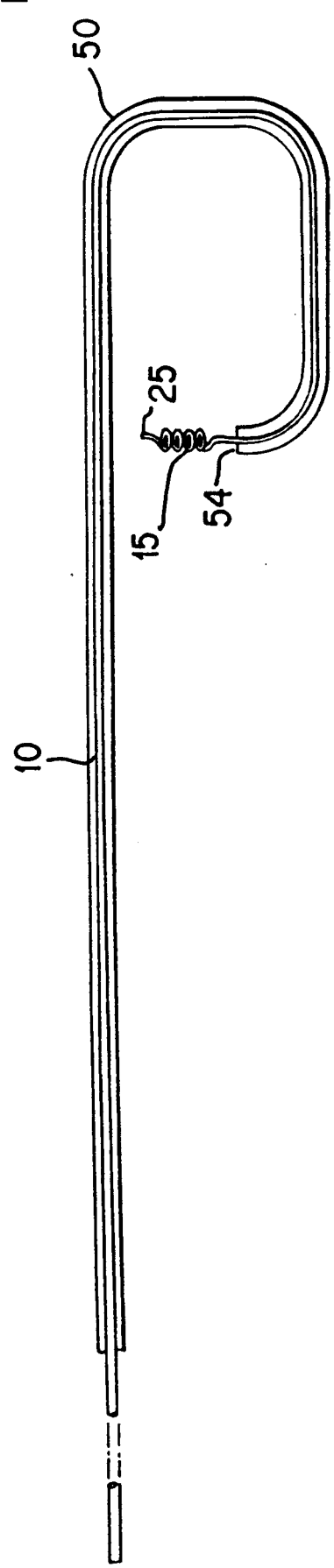
FIG. 4 is an illustration of the steerable guide wire with a pre-shaped catheter fitted over it and the helix at the distal end external to the catheter.

Referring to FIG. 4, the guide wire (5) may be used with a preshaped catheter (50) of proportional dimensions. FIG. 4 shows a guide wire disposed in a preshaped catheter (50) having the helix (15), which is located near the distal end (12) of the wire shaft (10), extended out from the distal opening (54) of the catheter (50).

FIGS. 5 and 6 illustrate the invention in operation. In one mode of operation, a typical endoscopic retrogade cannulation procedure is performed on the patient using a thick, flexible, conventional guide wire (a "first" guide wire) having an approximate length of 400 centimeters and a diameter of 1 millimeter. This first guide wire is inserted into the common bile duct (80). Over this first guide wire a pre-shaped catheter (50) having an approximate length of 180 centimeters and a 7 French gauge diameter is passed until the distal end of the catheter (50) is "hooked" into the cystic duct opening (62).

The first guide wire is then withdrawn and the distal end (12) of the steerable guide wire (5) is inserted into the pre-shaped catheter (50). As the guide wire (5) is inserted into the catheter (50), the helix (15) is significantly, but not totally, straightened as depicted in FIG. 2.

Torsional (37) and longitudinal force can be applied to the removable clamp (35) located at the proximal end (14) of the guide wire (5) until the distal tip (25) is advanced through the catheter and into the cystic duct. The position of the removable clamp (35) can be adjusted along the guide wire (5) to accommodate the requirements of the user.

At this point, the helix (15) is partially or completely outside of the catheter (50) within the cystic duct (60). Rotational torque (37) is then gently applied to the guide wire (5). In a preferred embodiment, the torque is applied using the steering means (40) on the removable clamp (35). As rotational torque (37) is applied, the coils (20) of the helix (15) catch between the spiral folds (valves of Heister) (70) and advance the guide wire (5) along the folds (70) and into or near the gallbladder (95).

Once the guide wire (5) is within the gallbladder (95) or in the desired position, the pre-shaped catheter (50) can be gently withdrawn. The guide wire (5) is then in proper position for advanced stages of the procedure, for example to allow a mini-endoscope to be passed over it and into the gallbladder (95) for diagnosis and treatment. Such a mini-endoscope could be used to directly visualize the cystic duct (60) and gallbladder (95) pathology, or facilitate the extraction of brushings or biopsies from benign or malignant gallbladder lesions.

In addition, laser or electrohydrolic probes could be passed directly over the guide wire (5) or through an endoscope to fragment gallstones in the gallbladder. The guide wire (5) itself may be used to open a previously blocked cystic duct (60) and allow for medical dissolution of gallstones with or without adjuvant extracorporeal shock wave lithotripsy. Furthermore, the guide wire (5), once positioned in the gallbladder (95), can be used to facilitate the passage of a large 5 or 7 French gauge catheter over it. This size catheter may be used to infuse a gallstone dissolution agent and aspirate gallstone dissolution products, sample gallbladder bile directly for diagnostic or investigational purposes, or inject contrast into the gallbladder (95) to obtain a cholecystogram or air contrast cholecystrogram.

Removal of the guide wire (5) is accomplished by reversing the procedures explained above. Rotational force (37) is applied to the steering means (40) located on the proximal end (14) of the guide wire (5) in a reversed direction to negotiate the guide wire (5) back through the cystic duct (60) and into the common bile duct (80) without causing trauma to the valves of Heister. The guide wire (5) and the catheter (50) are then both removed from the patient.

The foregoing description of the preferred embodiments of the invention has been presented for purposes of illustration and description. It is not intended to be exhaustive or to limit the invention to the precise form disclosed, and obviously many modifications and variations are possible in light of the above teaching. For example, the guide wire (5) may be configured having other than a cylindrical cross-section. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A steerable guide wire comprising,
   a) a flexible wire shaft having a proximal end and a distal end; and
   b) means formed by the distal end of the flexible wire shaft for navigating and advancing the guide wire by contacting the walls of a vessel in corkscrew-type fashion.

2. The steerable guide wire of claim 1 wherein the length of said guide wire is between 10 cm and 10 m, and the diameter of said flexible wire shaft is between 0.2 mm–3.0 mm.

3. A steerable guide wire of claim 2, having means for manipulation of said guide wire secured to the guide wire near its proximal end.

4. The steerable guide wire of claim 3, wherein said means for manipulation of said guide wire comprises a removable clamp for communicating torque and steering forces to said clamp and to said guide wire.

5. The steerable guide wire of claim 2, wherein said means for navigating and advancing terminates at a soft, flexible distal tip.

6. The steerable guide wire of claim 1, wherein said means for navigating and advancing is a helix having at least one coil.

7. A steerable guide wire, comprising a flexible wire shaft having a proximal and a distal end, said shaft forming at least one coil near the distal end of said guide wire for navigating and advancing the guide wire by contacting the walls of a tortuous duct as said guide wire is rotated in a corkscrew-type fashion.

8. The steerable guide wire of claim 7, wherein said guide wire has a length of between 10 cm and 10 meters, said flexible wire shaft having a diameter of 0.20 mm to 3.0 mm and each of said at least one coils has an outer diameter of 0.50 mm to 2.5 cm.

9. The steerable guide wire of claim 8, wherein said guide wire has a low friction coating.

10. The steerable guide wire of claim 8 having means for manipulation of said guide wire comprised of a removable clamp wherein said clamp can be secured to said guide wire so that torsional force applied to said clamp is communicated to said guide wire.

11. A steerable guide wire for cannulation of the gallbladder, comprising:
    a) a flexible wire shaft of circular cross-section having a diameter between 0.20 mm and 1.25 mm, said flexible wire shaft having a proximal end, a distal end, and a total length of from 50 cm to 1,000 cm; and
    b) at least one coil formed by the flexible wire shaft near the distal end of said guide wire for navigating and advancing the guide wire through the crescentic folds of the cystic duct by contacting the walls of said duct in a corkscrew-type fashion, said at least one coil having an outer diameter greater than the diameter of the distal end of said flexible wire shaft.

12. The steerable guide wire for cannulation of the gallbladder as recited in claim 11, further comprising a removable clamp secured to the guide wire near its proximal end, said removable clamp having means for communicating longitudinal and torsional forces to said guide wire.

13. The steerable guide wire for cannulation of the gallbladder as recited in claim 11, wherein the flexible wire shaft has a tapered section near its distal end, wherein the circular cross-section of said wire shaft tapers to a diameter between 0.10 mm and 1.25 mm at the distal end.

14. The steerable guide wire for cannulation of the gallbladder as recited in claim 11 wherein said at least one coil forms a helix near the distal end of the flexible wire shaft, said helix terminating with a soft, flexible distal tip located on the distal side of said helix.

15. The steerable guide wire for cannulation of the gallbladder as recited in claim 11 wherein said flexible wire shaft has a low friction surface.

* * * * *